(12) United States Patent
Goldberg et al.

(10) Patent No.: US 6,770,063 B2
(45) Date of Patent: Aug. 3, 2004

(54) THORACIC VENT KIT

(75) Inventors: Robert Goldberg, Chicago, IL (US); Stephen Ovcharchyn, Naperville, IL (US); Jim Sarns, Naperville, IL (US)

(73) Assignee: Uresil, L.P., Skokie, IL (US)

( * ) Notice: Subject to any disclaimer, the term of this patent is extended or adjusted under 35 U.S.C. 154(b) by 275 days.

(21) Appl. No.: 10/127,954

(22) Filed: Apr. 23, 2002

(65) Prior Publication Data

US 2003/0199828 A1 Oct. 23, 2003

(51) Int. Cl.⁷ .............................. A61M 1/00
(52) U.S. Cl. .................... 604/326; 604/323; 604/540; 604/533
(58) Field of Search ................... 604/540, 319, 604/323, 326, 533, 534, 537, 538, 539, 284

(56) References Cited

U.S. PATENT DOCUMENTS

| | | | |
|---|---|---|---|
| 1,202,971 A | * 10/1916 | Daiber | 433/185 |
| 4,063,556 A | * 12/1977 | Thomas et al. | 604/318 |
| 4,273,126 A | * 6/1981 | Grane et al. | 604/319 |
| 4,664,660 A | 5/1987 | Goldberg et al. | |
| 4,838,873 A | * 6/1989 | Landskron et al. | 604/533 |
| 4,915,691 A | * 4/1990 | Jones et al. | 604/73 |
| 4,944,724 A | 7/1990 | Goldberg et al. | |
| 5,084,034 A | * 1/1992 | Zanotti | 604/319 |
| 5,356,386 A | 10/1994 | Goldberg et al. | |
| 5,389,090 A | * 2/1995 | Fischell et al. | 604/528 |
| 5,827,228 A | * 10/1998 | Rowe | 604/167.02 |
| 6,059,759 A | * 5/2000 | Mottola et al. | 604/264 |
| 6,391,009 B1 | * 5/2002 | Dorado | 604/319 |
| 6,575,946 B2 | * 6/2003 | Sealfon | 604/323 |
| 6,673,055 B2 | * 1/2004 | Bemis et al. | 604/319 |

* cited by examiner

*Primary Examiner*—John J. Calvert
*Assistant Examiner*—Michael Bogart
(74) *Attorney, Agent, or Firm*—Marshall, Gerstein & Borun LLP

(57) ABSTRACT

A thoracic vent kit has a reservoir and an introducing port and a catheter port. A removable cannula is small enough to fit in the catheter, but has an internal diameter that can accommodate a flexible guide wire. The cannula has a beveled tip and a luer threaded cap at the opposite end. A removable plug has a chamfer that can be used to seal the luer passage.

15 Claims, 3 Drawing Sheets

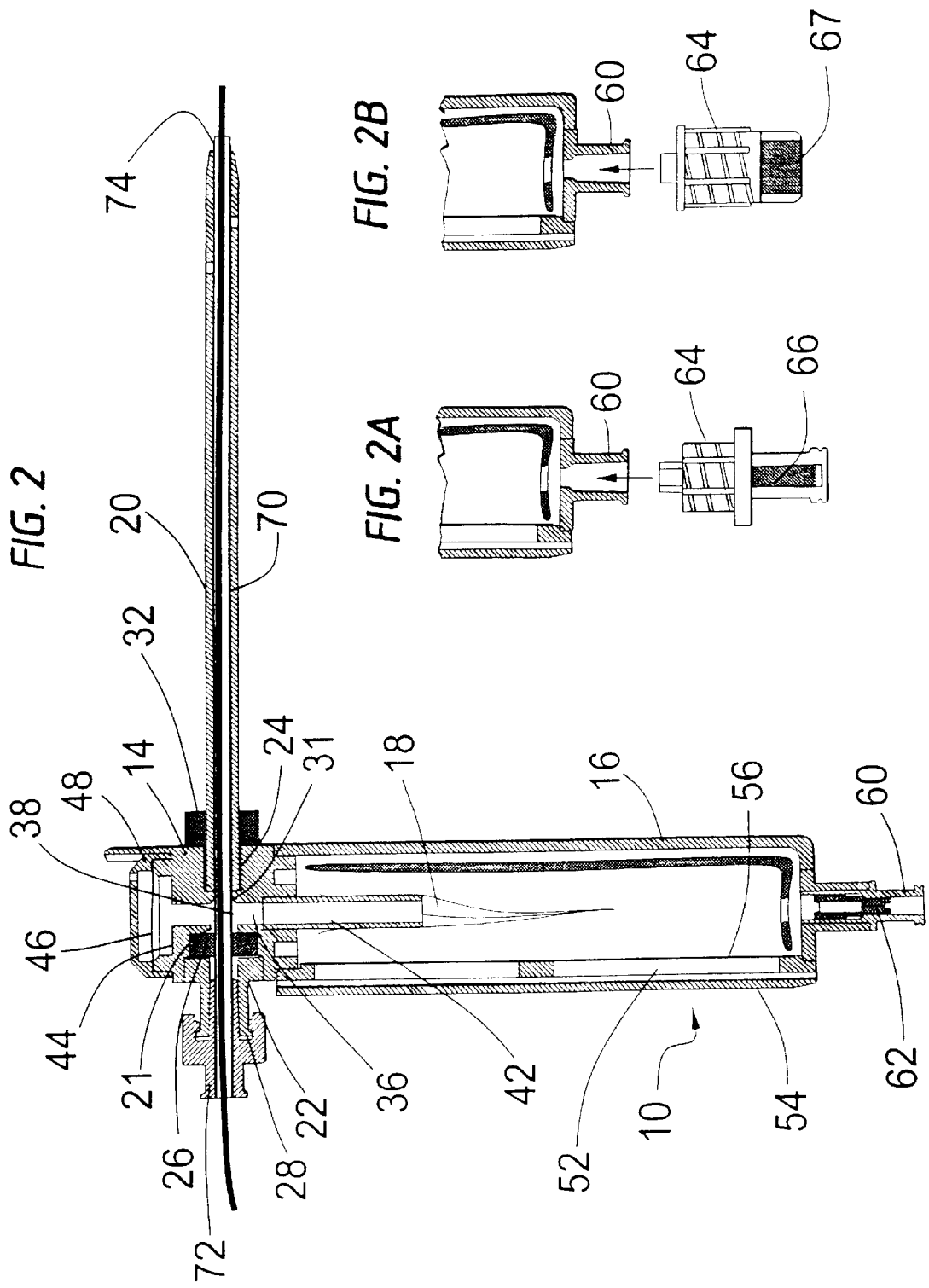

THORACIC VENT KIT

BACKGROUND OF THE INVENTION

This invention relates generally to medical devices for draining fluids from body cavities. More particularly, it relates to an improved vent for positively locating a body cavity that has fluctuating fluid pressure and draining the cavity.

One vent for draining fluids from body cavities, particularly the pleural cavity, is described in U.S. Pat. No. 4,664,660. The vent described in that patent includes a vented housing having a fluid-receiving chamber, an anti-reflux valve mounted to the housing, and a catheter that extends from the housing and is in communication with the chamber through the anti-reflux valve. The apparatus is used by first inserting a solid trocar into the end of the catheter. A skin incision is then prepared and the trocar/catheter assembly is introduced into the pleural space through the incision. When the trocar is removed from the catheter, fluid drains from the pleural cavity through the catheter and the vented housing.

Another apparatus for draining fluids from body cavities, particularly liquids from the pleural cavity, is disclosed in U.S. Pat. No. 4,447,235. The apparatus described in that patent includes a catheter/hollow needle assembly that is inserted into the pleural cavity. During the insertion procedure, a vacuum is maintained in the needle with a syringe. As a result, liquid enters the syringe when the needle enters the pleural space, and can be observed by the surgeon.

U.S. Pat. No. 4,404,924 describes a medical suction device that has an indicator flag to signal the pressure being developed by the device. The indicator flag is designed to stand upright when the pressure in the device is relatively high and to collapse when suction is developed.

U.S. Pat. No. 4,164,938 describes a device for diagnosing the presence of a tension pneumothorax. The device includes a sleeve with a needle at one end for puncturing the chest wall. The needle extends into the pleural cavity and a diaphragm at the other end of the device expands when the pressure in the pleural cavity is greater than atmospheric.

U.S. Pat. Nos. 4,944,724 and 5,356,386 disclose devices used to drain fluids from the pleural cavity. The fluids are drained through a passage that extends from a catheter to a one-way valve. The catheter is inserted with a furrowed trocar that permits fluid communication between the tip of the catheter and an indicator on the device. When the catheter enters a body cavity in which there is fluctuating fluid pressure, the fluctuating pressure causes the indicator to deflect. After the trocar is removed, a seal prevents ambient air from entering the device.

Some physicians feel that using a trocar to introduce a catheter imposes a risk of damaging the heart, lung, or surrounding tissue. This risk can be greatly reduced by using a flexible guide wire for introducing the catheter. However, such guide wires cannot readily be passed through the seal of the devices shown in the U.S. Pat Nos. 4,664,660; 4,944,724; and 5,356,386; patents.

SUMMARY OF THE INVENTION

The present invention provides a thoracic vent kit that enables a physician to introduce the thoracic vent over a flexible guide wire. Like some prior vents, the vent has a reservoir and a manifold with an introducing port, a catheter port, and a linear passage extending from the introducing port to the catheter port. It also has a second passage extending from an intersection on the linear passage to an evacuation port. The manifold provides a fluid path that extends from a catheter through the catheter port, a portion of the linear passage, the second passage, the evacuation port, and a one-way valve to the reservoir. A seal is provided on the linear passage between the intersection and the introducing port.

Unlike prior known thoracic vent kits, the present invention may include a removable cannula that is small enough to fit in the catheter, but also has an internal diameter that can accommodate a flexible guide wire. The cannula may have a beveled tip at its distal end, and a luer threaded cap at a proximal end. A removable plug may also be included in the kit. The plug may have a shaft with a chamfer that has a maximum diameter that is greater than the diameter of the linear passage between the intersection and the catheter port, and a terminal dimension that is less than that diameter of the linear passage. The opposite end of the plug may be configured for connecting the plug to the introducing port while the chamfer seals the air path.

BRIEF DESCRIPTION OF THE DRAWINGS

The invention may be better understood by referring to the accompanying drawings, in which:

FIG. 2 is a sectional elevational view of the side of the vent seen in FIG. 1;

FIGS. 2A and 2B are views of alternate arrangements for the bottom of the vent seen in FIG. 2;

DESCRIPTION OF THE PREFERRED EMBODIMENTS

Figure 1:
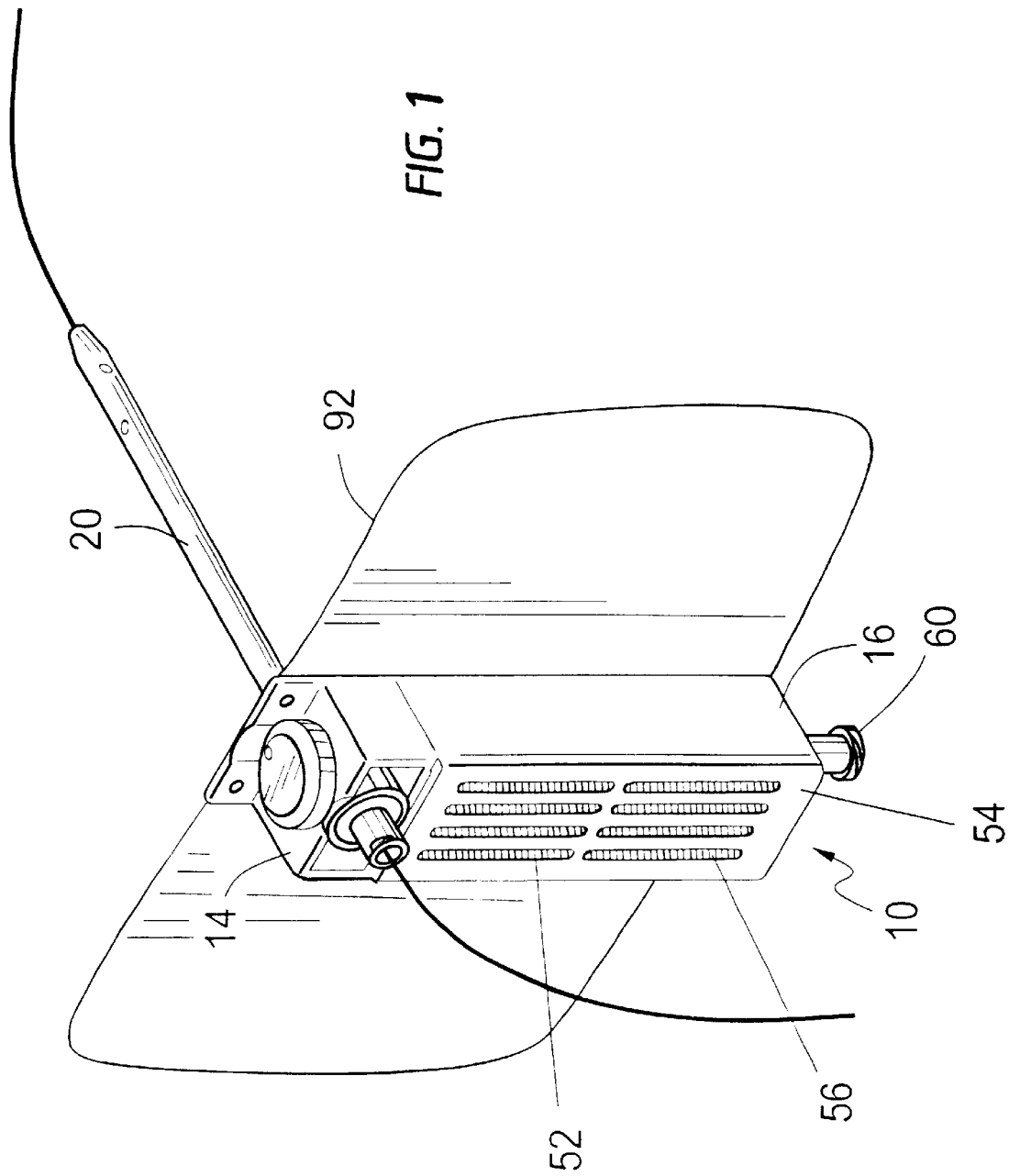
FIG. 1 is an exploded perspective view of a thoracic vent in accordance with the present invention, the vent being disposed on a guide wire for insertion of the catheter into a patient.

The vent kit of the present invention is intended to be used in locating and in moving fluids either into or out of body cavities such as the pleural cavity, the spinal epidural space, blood vessels, the gallbladder, the urinary bladder, the kidney pelvis, the brain ventricles and the brain subdural and epidural spaces. However, for purposes of illustration, the discussion below is directed primarily to an embodiment of the invention particularly suited for locating and draining fluids from the pleural cavity.

One embodiment of a vent kit in accordance with the present invention is illustrated in the figures. The kit includes vent unit 10 (seen in FIGS. 1 and 2) that has a manifold 14, a reservoir 16, a one-way valve 18, and a catheter 20. The illustrated kit also includes a removable cannula 30 (seen in FIG. 3) and a removable plug 40 (seen in FIG. 4).

As seen in FIG. 2, the manifold 14 on the vent unit 10 has a linear passage 21 that extends in a line from an introducing port 22 to a catheter port 24. A flexible seal 26 is disposed in the linear passage near the introducing port. The seal that is illustrated is made of a highly-resilient material such as latex, polyisoprene or silicone. While not necessary to the invention, the figures show the introducing port with a luer lock 28. In the figures, the diameter of a portion of the linear passage near the introducing port is greater than the diameter of the linear passage near the catheter port, and sealing walls 31 are provided inside the flexible seal. The variation in diameter and the sealing walls are not necessary, but can provide an additional benefit described later.

The catheter 20 is connected to the catheter port 24. The catheter that has been illustrated is a tube of a resilient polymer, such as polyurethane or silicone rubber. Alternatively, it could be formed from a stainless steel spring core covered with an elastomer. The catheter is sealed into the catheter port to prevent air or other fluids from entering the vent unit 10. A seal cuff 32 may also be provided around the catheter, adjacent the wall of the vent unit that will abut the patient's body. The cuff, which is preferably a sponge silicone or other resilient material, may prevent tissue emphysema by sealing the perimeter of the catheter at the site where the catheter enters the body.

The manifold 14 has a second passage 36 that is in fluid communication with the linear passage 21. The second passage extends from an intersection 38 on the linear passage to an evacuation port 42. In the figures, the second passage also extends upwardly from the intersection to a top surface 44 on the manifold. There, the second passage is in fluid communication with an indicator 46 that can be used to signal when the tip of the catheter has entered the pleural cavity.

In the illustrated embodiment of the invention, the indicator 46 is a flat resilient membrane that deflects upward with positive pressure and deflects downward with negative pressure. The sensitivity of the indicator can be adjusted as necessary by varying, for example, the material from which it is made, as well as its size or shape, or its wall thickness. Alternatively, the indicator could take the form of a signal dome. A clear cover 48 on the top of the manifold holds and protects the indicator.

A fluid path extends from the catheter port 24, through a portion of the linear passage 21 and through the second passage 36 to the evacuation port 42. The fluid path allows fluid to vent from the pleural space to the evacuation port.

The reservoir 16 is connected to the manifold 14. The one-way valve 18 separates the fluid path within the manifold 14 from the reservoir. In the figures, the one-way valve 18 is a film valve. Such a film valve can be made of two pieces of virtually any type of plastic film, such as polyethylene, mylar, nylon or polyvinyl chloride, as well as laminates of these materials, and is very responsive to even slight pressures. Other one-way valves, such as the "Heimlich valve" described in U.S. Pat. Nos. 4,664,660 and 3,463,159, might also be used.

The reservoir 16 that has been illustrated is made of rigid, impervious material, such as an acrylic, ABS, polystyrene or polyvinyl chloride. As seen in FIG. 1, it has a series of elongated vent openings 52 located behind a protective faceplate 54. The faceplate is affixed to the vent unit 10 along its sides and is undercut to create a passage at the top and bottom through which gaseous fluids vent to the atmosphere. A hydrophobic filter 56 can be mounted behind the vent openings to prevent aqueous liquids from escaping the reservoir. The illustrated vent unit is very compact, standing about 4" tall and about 1" wide.

In the embodiment of the invention that is illustrated, the reservoir 16 has an optional drainage port 60. The drainage port can be used to drain liquids from the reservoir. The drainage port that has been illustrated comprises an optional syringe-activated valve 62 housed within the port. The drainage port has been shown on the bottom of the reservoir, but it could be positioned on the side of the reservoir. A cap 64 can be provided for the drainage port. The illustrated cap has an optional syringe-activated valve 66 as shown in FIG. 2A. FIG. 2B shows a pierceable septum 67 that can be used as an alternative.

Figure 3A:
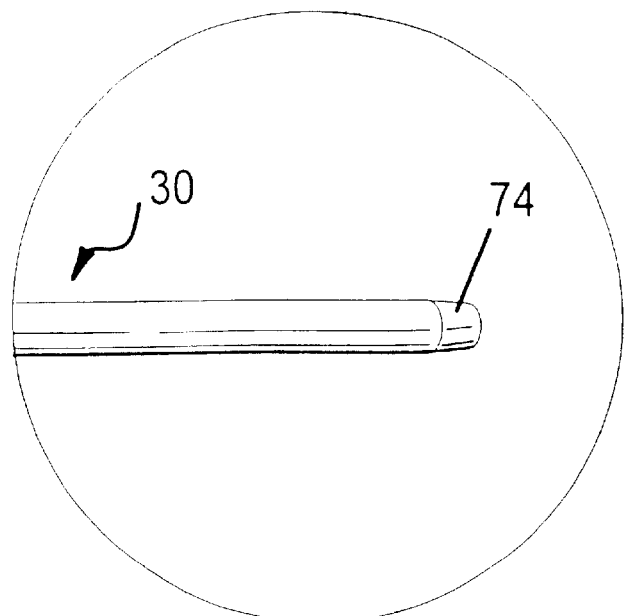
FIG. 3A is an enlarged view of the tip of the cannula seen in FIG. 3.
Figure 3:
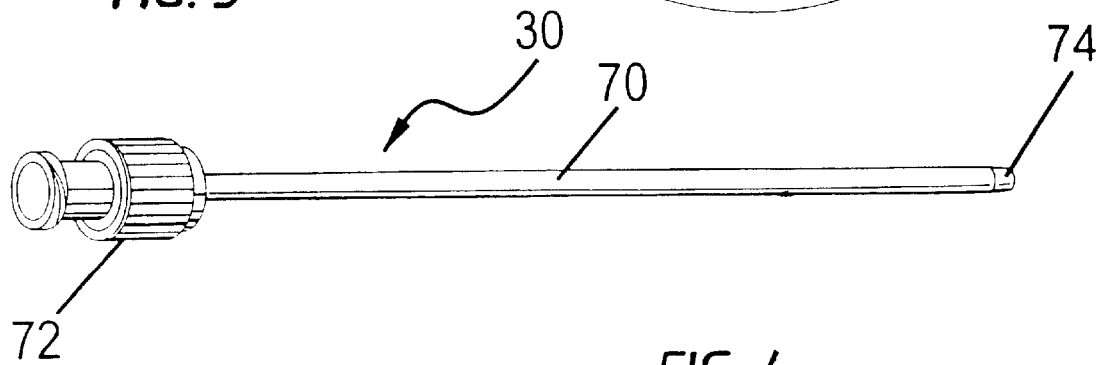
FIG. 3 is an elevational view of a removable cannula seen in FIG. 1.

The removable cannula 30, seen in FIG. 3, can be used to insert the catheter 20 into a patient along a guide wire. The removable cannula has a hollow shaft 70 with a luer threaded cap 72 at one end and a tip 74 at the other end. The shaft can be stiff, and can be made of stainless steel or a rigid thermoplastic such as nylon. The shaft has an internal diameter of at least about ½ mm, and is thus sized to accommodate the kinds of flexible guide wires commonly in use by physicians. The external diameter of the shaft is no greater than the diameter of the linear passage 21 in the manifold 14, and the internal diameter of the catheter 20. The illustrated shaft is about 4" long and has an external diameter of about 1/16".

To insert the catheter 20 using a guide wire, the tip 74 of the removable cannula 30 is inserted into the introducing port 22 of the vent unit 10. The shaft 70 of the cannula is passed through the proximal portions of the linear passage 21 and the seal 26 in the manifold 14, past the intersection 38 and into the catheter 20. Placed in this manner, the shaft of the cannula holds the seal open such that a guide wire can be freely passed through the entire manifold and catheter.

When the catheter 20 is in place in the patient, the cannula 30 can be withdrawn. As the tip 74 of the cannula is withdrawn through the seal 26, the seal closes. Once closed, the seal prevents air from entering the pleural space through the introducing port 22.

Preferably, the tip 74 of the removable cannula 30 is beveled at its distal end, as seen in FIG. 3A. When the cannula is fully inserted into the catheter 20, the beveled tip projects beyond the end 80 of the catheter, facilitating the passage of the catheter into a patient.

In the illustrated embodiment of the invention, the luer threaded cap 72 on the removable cannula 30 can be used to lock onto the luer lock 28 and on the introducing port 22 on the manifold 14, facilitating the insertion of the catheter 20.

Figure 4:
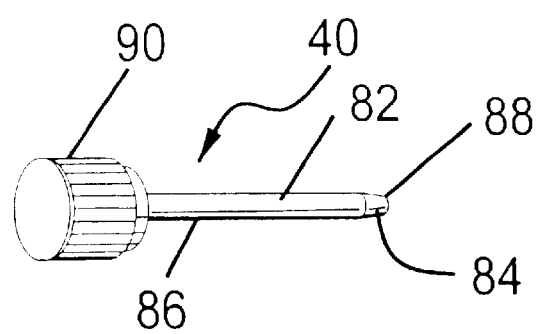
FIG. 4 is an elevational view of a removable plug for use with the vent seen in FIG. 1.

The removable plug 40 seen in FIG. 4 enables a health care provider to selectively prevent fluid from flowing through the vent unit 10. The illustrated plug has a shaft 82 that is made of a resilient material and has a chamfer 84 at its distal end. The shaft is long and thin enough to be inserted into the linear passage 21 through the introducing port 22 to seal the path between the intersection 38 and the catheter port 24. Preferably, the chamfer has a maximum diameter 86 that is greater than the diameter of the linear passage between the intersection and the catheter port, and a terminal diameter 88 that is less than that diameter of the linear passage. The chamfer can be pressed against the sealing walls 31 of the linear passage between the intersection and the catheter port, thus sealing the path and preventing fluid from leaving the pleural space through the vent unit. The illustrated plug has a shaft that is about ¾" long with a maximum diameter of about 3/32" and a terminal diameter of less than 1/64".

Preferably, the plug also has a luer threaded cap 90 that enables the plug to be connected to the introducing port 22 while the chamfer 84 seals the fluid path. Configured like this, the plug can be screwed onto the luer lock 28 on the introducing port 22 while the chamfer seals the air path.

In the illustrated embodiment of the invention, a self-adhesive strip 92 is attached to the exterior of the vent unit 10. The adhesive strip is covered by a protective release sheet that can be removed prior to installation of the catheter. The strip can then be applied to the patient's skin upon installation of the apparatus.

In treating spontaneous, traumatic or iatrogenic pneumothorax, or for evacuating air from the chest following thoracic surgery or percutaneous lung biopsy, the vent kit may be used as follows:

1. Select a site, preferably at the second interspace in the mid-clavicular line or at another appropriate location.
2. Prepare the site using standard procedure. Place a fenestrated drape over the site.
3. Infiltrate local anesthesia into the chest wall at the site indicated.
4. Using a scalpel, make a small incision at the selected site.
5. Place a guidewire into the site using standard technique. Tract over-dilation will ease placement.
6. Introduce the removable cannula 30 into the vent unit 10 through the introducing port 22. The distal end of the cannula 74 should extend slightly beyond the end 80 of the catheter.
7. Thread the guidewire through the removable cannula 30.
8. Peel away the center portions of the paper cover from the self-adhesive strip 92.
9. Introduce the removable cannula 30 and catheter 20 into the pleural space over the guidewire.
10. Stop advancing the cannula/catheter assembly when the catheter end has entered the pleural cavity.
11. Advance the catheter over the guidewire while holding the cannula stationary until the full length of the catheter is introduced into the pleural cavity.
12. Remove the cannula and the guidewire from the vent unit.
13. Check the indicator 46 for proper function.
14. Peel away the paper from the side flaps of the self-adhesive strip 92 and adhere the strip to the chest wall. Make sure the chest surface is dry.
15. If the patient is expected to be active, place sutures through the adhesive patch and suture holes on top of the device to further anchor it in place.
16. Fluids collected in the reservoir 16 can be extracted using the drainage port 60.
17. The fluid passage leading from the catheter port 24 can be sealed by placing the plug 40 into the introduction port 22.
18. When the pneumothorax is resolved, the indicator will stop fluctuating. Confirm and the vent unit can be removed.

What is claimed is:

1. A medical vent kit comprising:
  a manifold with an introducing port, a catheter port, a linear passage extending from the introducing port to the catheter port, a second passage extending from an intersection on the linear passage to an evacuation port; a fluid path extending from the catheter port and through a portion of the linear passage and through the second passage; and a seal on the linear passage between the intersection and the introducing port;
  a catheter connected to the catheter port;
  a reservoir connected to the evacuation port;
  a one-way valve connected to the evacuation port; and
  a removable cannula with a grip at a proximal end, the cannula having an internal diameter of at least about ½ mm, and an external diameter that is no greater than the diameter of the linear passage and no greater than the internal diameter of the catheter; and
  a removable plug that has (1) a shaft with a chamfer that has a maximum diameter that is greater than the diameter of the linear passage between the intersection and the catheter port, and a terminal dimension that is less than that diameter of the linear passage, and (2) connecting means for connecting the plug to the introducing port while the chamfer seals the air path.

2. A medical vent kit as recited in claim 1, in which:
  the kit further comprises an indicator in communication with the air path.

3. A medical vent kit as recited in claim 1, in which the reservoir has a drainage port.

4. A medical vent kit as recited in claim 1, in which:
  the reservoir has a drainage port; and
  the kit further comprises a cap for the drainage port.

5. A medical vent kit as recited in claim 1, in which:
  the kit further comprises a cap for the drainage port, the cap having a syringe-activated valve.

6. A medical vent kit as recited in claim 1, in which:
  the reservoir has a drainage port; and
  the drainage port comprises a syringe-activated valve housed within the reservoir.

7. A medical vent kit comprising:
  a manifold with an introducing port, a catheter port, a linear passage extending from the introducing port to the catheter port, a second passage extending from an intersection on the linear passage to an evacuation port; a fluid path extending from the catheter port and through a portion of the linear passage and through the second passage; and a seal on the linear passage between the intersection and the introducing port;
  a catheter connected to the catheter port;
  a reservoir connected to the evacuation port;
  a one-way valve connected to the lower port; and
  a removable cannula with a grip at a proximal end, the cannula having an internal diameter of at least ½ mm, and an external diameter that is no greater than the diameter of the linear passage and the internal diameter of the catheter.

8. A medical vent kit as recited in claim 3, in which:
  the cannula has a distal end with a beveled tip.

9. A medical vent kit as recited in claim 3, in which:
  the cannula further comprises connecting means for connecting the cannula to the introducing port.

10. A medical vent kit as recited in claim 3, in which:
  the cannula further comprises a luer lock.

11. A medical vent kit comprising:
  a manifold with an introducing port, a catheter port, a linear passage extending from the introducing port to the catheter port, a second passage extending from an intersection on the linear passage to an evacuation port; an air path extending from the catheter port and through a portion of the linear passage and the second passage; and a seal on the linear passage between the intersection and the introducing port;
  a catheter connected to the catheter port;
  a reservoir connected to the evacuation port;
  a one-way valve connected to the evacuation port; and
  a removable plug that has (1) a shaft with a chamfer that has a maximum diameter that is greater than the diameter of the linear passage between the intersection and the catheter port, and a terminal dimension that is less than that diameter of the linear passage, and (2) connecting means for connecting the plug to the introducing port while the chamfer seals the air path.

12. A medical vent kit as recited in claim 11, in which:

the shaft of the plug is made of a resilient material.

13. A medical vent kit as recited in claim 11, in which:

the diameter of a portion of the linear passage between the intersection and the introducing port is greater than the diameter of the linear passage between the intersection and the catheter port.

14. A medical vent kit as recited in claim 11, in which:

the air path has a beveled edge on the linear passage, near the intersection.

15. A medical vent kit as recited in claim 11, in which:

the connecting means enables the chamfer to be compressed against the linear passage between the catheter port and the intersection.

\* \* \* \* \*